United States Patent [19]

Widemire

[11] Patent Number: 5,782,788
[45] Date of Patent: Jul. 21, 1998

[54] WOUND DRESSING

[76] Inventor: DeWitt P. Widemire, 3369 Ching Dairy Rd., Mobile, Ala. 36618-4433

[21] Appl. No.: 822,698

[22] Filed: Mar. 21, 1997

[51] Int. Cl.$^6$ ...................................... A61F 5/00
[52] U.S. Cl. .................. 602/48; 602/43; 602/54; 602/57
[58] Field of Search ............... 602/41–59; 128/888, 128/889; 604/304–309; 607/108–112

[56] References Cited

U.S. PATENT DOCUMENTS

| | | | |
|---|---|---|---|
| 2,934,066 | 4/1960 | Stowasser | 602/43 |
| 3,830,908 | 8/1974 | Klippel et al. | 424/28 |
| 4,446,124 | 5/1984 | Fox, Jr. et al. | 424/27 |
| 4,599,226 | 7/1986 | Fox, Jr. et al. | 424/27 |
| 4,606,962 | 8/1986 | Reylek et al. | 424/148 |
| 4,728,323 | 3/1988 | Matson | 604/304 |
| 4,767,401 | 8/1988 | Seiderman | 604/20 |
| 4,906,466 | 3/1990 | Edwards et al. | 424/78 |
| 5,052,381 | 10/1991 | Gilbert et al. | 206/440 |
| 5,320,908 | 6/1994 | Sodervall et al. | 428/461 |
| 5,330,452 | 7/1994 | Zook | 604/307 |
| 5,487,889 | 1/1996 | Eckert et al. | 424/93.1 |

Primary Examiner—Richard J. Apley
Assistant Examiner—Kim M. Lee
Attorney, Agent, or Firm—Richard L. Miller, P. E.

[57] ABSTRACT

An improved adhesive pad having an elastic substrate with an elastic layer thereon, a gauze pad affixed to the substrate by the layer of adhesive on the substrate, and release sheets releasibly covering and protecting the layer of adhesive on the substrate and the gauze pad prior to use, wherein the improvement comprises a layer of silver foil affixed to the gauze pad that inhibits growth of bacteria, viruses, and fungus in wounds by having its positive ions attracted to the negative DC field or an extremity so as to allow the silver ions to bind avidly to proteins and provide further protection against additional invasion of the bacteria, viruses, or fungi. The layer of silver foil can be plain, perforated, or embossed.

2 Claims, 1 Drawing Sheet

WOUND DRESSING

BACKGROUND OF THE INVENTION

1. Field of the Invention

The present invention relates to an adhesive pad. More particularly, the present invention relates to an adhesive pad that utilizes the negative human DC field pattern to kill bacteria and the like.

2. Description of the Prior Art

The treatment of wounds in mammals, both animals and humans, has historically involved a simple passive bandage which provides physical protection and, to some extent, reduces infection. The treatment has progressed from this simple bandage to more active treatments.

Numerous innovations for medicating devices have been provided in the prior art that will be described. Even though these innovations may be suitable for the specific individual purposes to which they address, however, they differ from the present invention.

FOR EXAMPLE, U.S. Pat. No. 4,446,124 to Fox, Jr. et al. teach animal tissue and the like having silver sulfadiazine incorporated therein for use as a covering for burns and/or wounds. The silver sulfadiazine is incorporated in the tissue by soaking the tissue in an ammoniacal silver sulfadiazine solution or suspension. When the silver sulfadiazine is so incorporated in the tissue via an ammonium solution, more silver is found to be present than would normally be expected and the effectiveness of the thus treated tissue as a wound covering increases.

ANOTHER EXAMPLE, U.S. Pat. No. 4,599,226 to Fox, Jr. et al. teach animal tissue and the like having silver sulfadiazine incorporated therein for use as a covering for burns and/or wounds. The silver sulfadiazine is incorporated in the tissue by soaking the tissue in an ammoniacal silver sulfadiazine solution or suspension. When the silver sulfadiazine is so incorporated in the tissue via an ammonium solution, more silver is found to be present than would normally be expected and the effectiveness of the thus treated tissue as a wound covering increases.

STILL ANOTHER EXAMPLE, U.S. Pat. No. 4,906,466 to Edwards et al. teach an antimicrobial composition for topical use or for incorporation into a coating or structural composition comprises an antimicrobial silver compound, preferably silver chloride, deposited on a physiologically inert oxidic synthetic particulate support material in particulate form. A preferred support material is titania containing one or more of the crystalline forms anatase, rutile, and brookite.

YET ANOTHER EXAMPLE, U.S. Pat. No. 5,330,452 to Zook teaches a topical medicating device that includes a transparent viscoelastic gel pad having one or more pharmacologically-active substances incorporated therein. A sheet of transparent, impermeable, and elastic material provides an occlusive layer adjacent to the upper surface of the viscoelastic gel pad. An elastic retaining ring perimetrically surrounds the viscoelastic gel pad to prevent migration due to external pressure. And, a porous meshwork is attached to the elastic retaining ring so as to additionally anchor the gel pad from migration. The porous meshwork member may be located at the surface of the viscoelastic gel pad opposite the aforementioned occlusive covering sheet, or may run through the viscoelastic gel pad in its anchoring function. The viscoelastic gel pad, occlusive covering sheet, and retaining ring with porous meshwork may be affixed to a target skin surface of the patient by an adhesive tape bandage with a visual access opening. The adhesive bandage may by formed to integrally include the impermeable occlusive layer adjacent to the surface of the viscoelastic gel pad. As a topical anesthetic device, the liquid fraction of the viscoelastic gel pad may be a solution of alcohol and water, preferably, but not limited to, 70% ethyl alcohol, wherein is dissolved 10% to 40%, by weight, of Lidocaine, U.S.P./N.F.

FINALLY, STILL YET ANOTHER EXAMPLE, U.S. Pat. No. 5,487,889 to Eckert et al. teach a biological bandage comprising an envelope enclosing cells which secrete biologically active cellular products such as growth factors, which promote the healing of wounds. The envelope is further comprised of a permeable bottom membrane through which the cellular product diffuses, and a top membrane. Preferably the bandage has a separator interposed between the two membranes. This invention also relates to a method for treating wounds. The bandage provides a continuous, uniform source of fresh cellular product.

It is apparent that numerous innovations for medicating devices have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an improved adhesive pad that avoids the disadvantages of the prior art.

ANOTHER OBJECT of the present invention is to provide an improved adhesive pad that is simple and inexpensive to manufacture.

STILL ANOTHER OBJECT of the present invention is to provide an improved adhesive pad that is simple to use.

BRIEFLY STATED, YET ANOTHER OBJECT of the present invention is to provide an improved adhesive pad having an elastic substrate with an elastic layer thereon, a gauze pad affixed to the substrate by the layer of adhesive on the substrate, and release sheets releasibly covering and protecting the layer of adhesive on the substrate and the gauze pad prior to use, wherein the improvement comprises a layer of silver foil affixed to the gauze pad that inhibits growth of bacteria, viruses, and fungus in wounds by having its positive ions attracted to the negative DC field of an extremity so as to allow the silver ions to bind avidly to proteins and provide further protection against additional invasion of the bacteria, viruses, or fungi. The layer of silver foil can be plain, perforated, or embossed.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows.

LIST OF REFERENCE NUMERALS UTILIZED IN THE DRAWING

Figure 1:
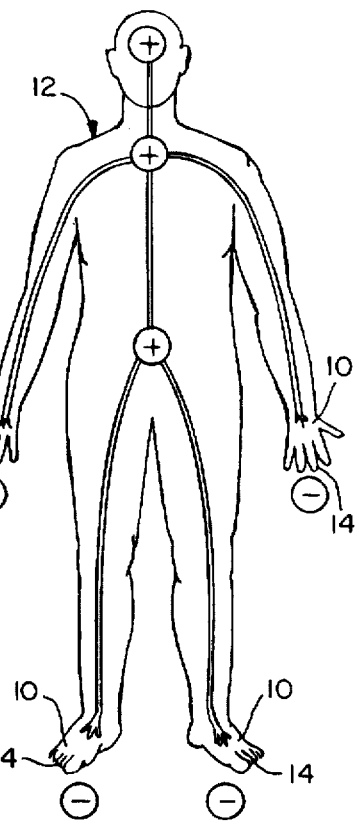
FIG. 1 is a diagrammatic view illustrating the human DC field pattern of a typical person.

Preferred Embodiment 10 body extremities
12 body
14 negative DC field
20 improved adhesive pad of the present invention
21 body extremity wound
22 substrate
24 substrate layer of adhesive
26 gauze pad
28 layer of silver foil
30 release sheets

First Alternate Embodiment 120 improved adhesive pad of the present invention
128 layer of foil

Second Alternate Embodiment 220 improved adhesive pad of the present invention
228 layer of foil

DETAILED DESCRIPTION OF THE PREFERRED EMBODIMENT

Referring now to the figures in which like numerals indicate like parts, and particularly to FIG. 1, the negative DC field of the body extremities 10 of the body 12 are shown at 14.

Figure 2:
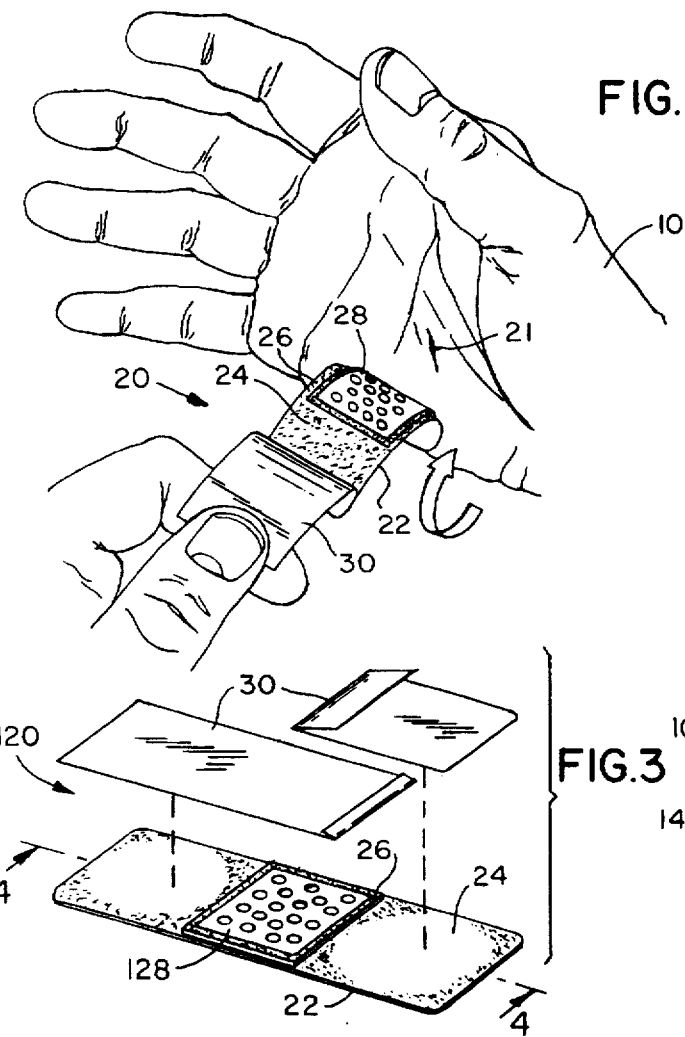
FIG. 2 is an enlarged diagrammatic perspective view of the preferred embodiment of the present invention having a plain silver foil layer and being applied to a wound.

The configuration of the improved adhesive pad 20 of the present invention can best be seen in FIG. 2, and as such will be discussed with reference thereto.

The improved adhesive pad 20 covers a body extremity wound on the body extremity 10 and includes a substrate 22 that is elastic and has a center and a substrate layer of adhesive 24 thereon.

The improved adhesive pad 20 further includes a gauze pad 26 that is affixed preferably to the center of the substrate 22, by the substrate layer of adhesive 24 on the substrate 22.

The improved adhesive pad 20 further includes a layer of silver foil 28 that is plain and affixed preferably by adhesive, sewing or the like, to the gauze pad 26.

The layer of silver foil 28 inhibits the growth of bacteria, viruses, and fungus in wounds. Further, silver as an excellent conductor of heat, displaces the heat of the body and the inflection so as to expedite healing. The positive silver ions are attracted to the negative DC field of the body extremities with the silver ions binding rather avidly to proteins so as to provide further protection against additional invasion of the bacteria, viruses, or fungi as well as concentrating in the body of the invader.

The improved adhesive pad 20 further includes release sheets 30 that releasibly cover and protect the substrate layer of adhesive 24 on the substrate 22 and the gauze pad 26 prior to use.

Figure 3:
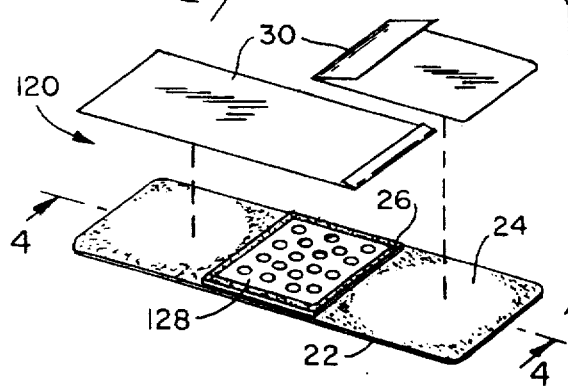
FIG. 3 is a diagrammatic perspective view of first alternate embodiment of the present invention having the foil layer perforated.
Figure 4:
FIG. 4 is a cross sectional view taken on line 4—4 in FIG. 3.

The configuration of the first alternate embodiment of the improved adhesive pad 120 can best be seen in FIGS. 3 and 4, and as such will be discussed with reference thereto.

The improved adhesive pad 120 is identical to the improved adhesive pad 20, except that the layer of foil 28 that is plain is replaced by a layer of foil 128 that is perforated so as to allow the serum seepage to be drawn into the gauze pad.

Figure 5:
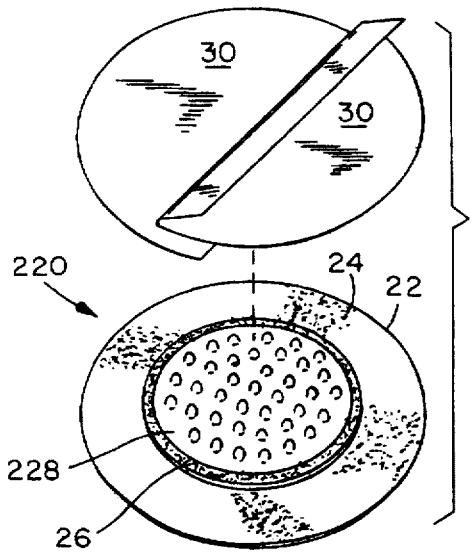
FIG. 5 is a diagrammatic perspective view of second alternate embodiment of the present invention having the foil layer embossed.

The configuration of the second alternate embodiment of the improved adhesive pad 220 can best be seen in FIG. 5, and as such will be discussed with reference thereto.

The improved adhesive pad 220 is identical to the improved adhesive pad 20, except that the layer of foil 28 that is plain is replaced by a layer of foil 228 that is embossed wherein the embossing functions as cooling fins that dissipate the heat from deep and open wounds while holding the fluids to the wound since research has shown that a wound heals faster if kept cool and that cells grow faster in body fluids approximating those of the body.

It will be understood that each of the elements described above, or two or more together, may also find a useful application in other types of constructions differing from the types described above.

While the invention has been illustrated and described as embodied in an improved adhesive pad, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An improved adhesive pad having an elastic substrate with an adhesive layer thereon, a gauze pad affixed to the substrate by the adhesive layer on the substrate, and release sheets releasibly covering and protecting the adhesive layer on the substrate and the gauze pad prior to use, wherein the improvement comprises a layer of silver foil affixed to the gauze pad that inhibits growth of bacteria, viruses, and fungus in wounds by having its positive ions attracted to the negative DC field of an extremity so as to allow the positive ions to bind avidly to proteins and provide further protection against additional invasion of the bacteria, viruses, or fungi; said layer of silver foil being embossed and functioning as cooling fins dissipating heat from deep and open wounds while holding fluids to the wounds since a wound heals faster if kept cool and cells grow faster in body fluids.

2. The improved adhesive pad as defined in claim 1, wherein said layer of silver foil is perforated so as to allow serum sepage to be drawn into the gauze pad.

\* \* \* \* \*